United States Patent
Meskens (10) Patent No.: US 8,369,959 B2
(45) Date of Patent: Feb. 5, 2013

(54) IMPLANTABLE MEDICAL DEVICE WITH INTEGRATED ANTENNA SYSTEM

(75) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 1131 days.

(21) Appl. No.: 12/131,832

(22) Filed: Jun. 2, 2008

(65) Prior Publication Data

US 2008/0300658 A1 Dec. 4, 2008

Related U.S. Application Data

(60) Provisional application No. 60/924,807, filed on May 31, 2007, provisional application No. 60/924,800, filed on May 31, 2007.

(51) Int. Cl.
*A61N 1/00* (2006.01)

(52) U.S. Cl. .................. 607/60; 607/57; 607/33

(58) Field of Classification Search .............. 607/57, 607/60, 33
See application file for complete search history.

(56) References Cited

U.S. PATENT DOCUMENTS

| | | | |
|---|---|---|---|
| 4,741,339 A | 5/1988 | Harrison et al. | |
| 5,597,380 A | 1/1997 | McDermott et al. | |
| 5,713,939 A * | 2/1998 | Nedungadi et al. | 607/33 |
| 6,141,588 A | 10/2000 | Cox et al. | |
| 6,748,094 B1 | 6/2004 | Tziviskos et al. | |
| 6,766,201 B2 | 7/2004 | Von Arx et al. | |
| 6,924,773 B1 | 8/2005 | Paratte et al. | |
| 7,020,298 B1 | 3/2006 | Tziviskos et al. | |
| 7,212,866 B1 * | 5/2007 | Griffith | 607/60 |
| 7,236,542 B2 * | 6/2007 | Matero | 375/295 |
| 7,894,915 B1 * | 2/2011 | Chitre et al. | 607/123 |
| 2002/0071581 A1 | 6/2002 | Leysieffer et al. | |
| 2005/0192648 A1 | 9/2005 | Killian et al. | |
| 2006/0290357 A1 * | 12/2006 | Campbell | 324/600 |
| 2007/0282394 A1 * | 12/2007 | Segel et al. | 607/57 |
| 2008/0154342 A1 * | 6/2008 | Digby et al. | 607/63 |

OTHER PUBLICATIONS

Extended European Search Report, Application No. 08010062.1 dated Mar. 27, 2009 (6 pages).

* cited by examiner

*Primary Examiner* — Niketa Patel
*Assistant Examiner* — William Levicky
(74) *Attorney, Agent, or Firm* — Kilpatrick, Townsend & Stockton, LLP.

(57) ABSTRACT

The present invention is related to active implantable medical devices comprising an antenna and a band diplexer connected to said antenna. The band diplexer comprises first filter means for a first signal to be transmitted and/or received in a first RF band and second filter means for a second signal to be transmitted and/or received in a second RF band. A method of bidirectional wireless communication is disclosed between an active implantable medical device and an external device, comprising the steps of: communicating unidirectionally from the external device to the implantable medical device over a first wireless link in a first RF band in the MI near-field and communicating unidirectionally from the implantable medical device to the external device over a second wireless link in a second RF band in the EM field.

53 Claims, 7 Drawing Sheets

IMPLANTABLE MEDICAL DEVICE WITH INTEGRATED ANTENNA SYSTEM

CROSS-REFERENCE TO RELATED APPLICATIONS

The present invention claims the benefit of U.S. Provisional Patent Application 60/924,807, filed May 31, 2007, which is hereby incorporated by reference herein.

BACKGROUND

1. Field of the Invention

The present invention relates generally to implantable medical devices and, more particularly, to an implantable medical device having an integrated antenna system.

2. Related Art

The efficacy of certain implantable medical devices has improved dramatically over the last few decades. As such, the type medical devices and the range of functions performed by implantable medical devices have increased over the years. For example, implantable medical devices may include an instrument, apparatus, appliance, material or other article, whether used individually, collectively or in combination with any accessory or software for its proper functioning, intended to be used to, for example, perform diagnosis, prevention, monitoring, treatment or management of a disease or injury or symptom thereof; to investigate, replace or modify of the anatomy or of a physiological process; or to control conception, and which does not achieve its principal intended action, and which may be assisted in its function by, pharmacological, chemical, immunological or metabolic techniques and substances.

An active medical device is any medical device relying for its functioning on a source of electrical energy or any source of power other than that directly generated by the human body or by gravity. An active implantable medical device (AIMD) is any active medical device which is intended to be totally or partially introduced, surgically or medically, into the human body or by medical intervention into a natural orifice, and which is intended to temporarily or permanently remain in the patient after the procedure.

SUMMARY

In accordance with one aspect of the present invention, an implantable medical device is disclosed, comprising: an internal antenna at which RF signals are transmitted to and/or received from one or more external devices; and a band diplexer, connected to the internal antenna, comprising: a first filter configured to filter for a differential-mode first signal to be transmitted and/or received in a first RF band, and a second filter configured to filter for a second signal to be transmitted and/or received in a second RF band, wherein the common-mode second RF band is higher in frequency than the differential-mode first RF band.

In accordance with another aspect of the invention, an implantable medical device having an implantable component configured to receive and/or generate internal data and/or power signals, is disclosed, the device comprising: an implantable antenna at which external radio frequency (RF) signals are transmitted to and/or received from one or more devices positionable external a patient's body; and a reciprocal frequency multiplexer/filter circuit configured to concurrently frequency-filter high- and low-frequency external RF signals received by the implantable antenna, and to concurrently frequency-multiplex common-mode high-frequency RF signals and differential-mode low-frequency RF signals to form high- and low-frequency external RF signals, respectively, for transmission to the one or more external devices via the internal antenna, the common-mode high- and differential-mode low-frequency RF signals corresponding to the internal signals generated by the implantable component.

BRIEF DESCRIPTION OF THE DRAWINGS

Embodiments of the present invention are described herein with reference to the accompanying drawings in which.

DETAILED DESCRIPTION

The present invention relates generally to an active implantable medical device (AIMD) having an integrated antenna system that enables wireless communication between external devices and the implantable device.

The increased use of wireless communication in and miniaturization of active implantable medical devices demands innovative, consistent and reliable designs of radio frequency (RF) system blocks and antennas. AIMDs are often shielded with a screening of titanium or other biocompatible material to decrease their vulnerability for trauma. As is well known in the art, antennas are generally positioned by preference outside any electrical or ferromagnetic shielding encapsulation of the implanted device to attain high efficiency power transfer and high reliability data transfer. Accordingly, the titanium RF shielding forces to position any type of antenna outside its shielding encapsulation.

The antenna characteristics for receiving energy are essentially the same as for transmission due to antenna reciprocity. A time-varying electrical current flowing in an antenna produces a corresponding electromagnetic field configuration that propagates through space in the form of electromagnetic waves. The total field configuration produced by an antenna may be decomposed into a far-field component, where the magnitudes of the electric and magnetic fields vary inversely with the distance from the antenna, and a near-field component with field magnitudes varying inversely with higher powers of the distance. The field configuration in the immediate vicinity of the antenna is primarily due to the near-field component (for example, magnetoinductive (MI) radio, Near Field Communication), while the field configuration at greater distances is due solely to the far-field component, also known as the electromagnetic far field propagation (electromagnetic radiation).

The EM far field propagation may be physically explained by the decomposed E-field and H-field components of the EM field, maintaining each other and forming planar waves. The MI field is a non-propagating quasi-static magnetic field and has very high field roll-off behaviour as a function of distance. Hence, the MI field is relevant only in the near-field. The electromagnetic (EM) field may be decomposed into a near-field component and a far-field component. The power of a plane wave in the EM far-field rolls off as a function of the inverse of the square of the distance from the source. The EM near-field may further be decomposed into an EM reactive near-field and an EM radiating near-field. As such, as used herein the term "far-field" refers to "EM far-field," while the term "near-field" refers to either or both an MI near-field and an EM near-field, and the term "reactive near-field" refers to either or both an MI field and a reactive EM near-field.

An antenna implemented in embodiments of the active implantable medical device of the present invention comprises one or more loops of an electrical conductor such as used in a coil antenna, loop antenna, etc. Such antennas are generally and collectively referred to herein as a closed-wire antenna. An external coil antenna may be coupled to such an internal coil antenna to transfer data such as telemetry, control data, signalling data and audio streaming. The data transfer with these types of antennas occurs in the MI near-field and at relatively lower frequencies such as, for example, frequencies below IS MHz. In the MI near-field, coil antennas are closely coupled and may also be used to transfer power to the AIMD.

Communication in the far-field may utilize an open-ended antenna tuned at a higher frequency band such as, for example, greater than 50 MHz, relying on propagating electromagnetic field characteristics. Examples of such an antenna include monopole and dipole antennas. An open-ended wire antenna most efficiently radiates energy if the length of the antenna is the sum of a quarter wavelength and an integral number of half-wavelengths of the driving signal. A dipole antenna, for example, is a conductor which has a total length equal to half the wavelength of the driving signal with its feed point in the middle. A monopole antenna may be a conductor with a length equal to one-quarter the wavelength of the driving signal situated with respect to a reflecting ground plane so that the total emitted and reflected field configuration resembles that of the dipole antenna. As described herein, embodiments of the present invention implement an antenna matching circuit to alter the effective electrical length of an antenna by adapting it with additional capacitance or inductance. This is described in greater detail below.

Aspects and embodiments of the present invention are generally directed to integrating an open-ended (EM-field) antenna into a closed-wire (near-field) antenna so as to obtain one single physical antenna which is able to concurrently operate over two separate frequency bands. The combined antenna allows for the establishment of concurrent bidirectional data communication links over a first, lower radio frequency band and over a second, upper radio frequency band. The two bands may be used simultaneously or consecutively in time for bidirectional communication between the AIMD and external devices operating in the lower RF band and the upper RF band. In certain embodiments of the invention, the combined antenna allows for the establishment of a forward unidirectional data communication link over a first, lower RF band (for example, from the external device towards an AIMD) and a backward unidirectional data communication link over a second, upper RF band (for example, from an AIMD towards an external device).

The first, lower radio frequency band lies preferably below 30 MHz, more preferably below 15 MHz. The second, upper frequency band lies preferably well above 15 MHz, more preferably well above 50 MHz (e.g. on the order of a few GHz). For the purposes of the present invention, the upper RF band signals are signals in the VHF (very high frequency), UHF (ultra high frequency), or higher frequency range.

Figure 1A:
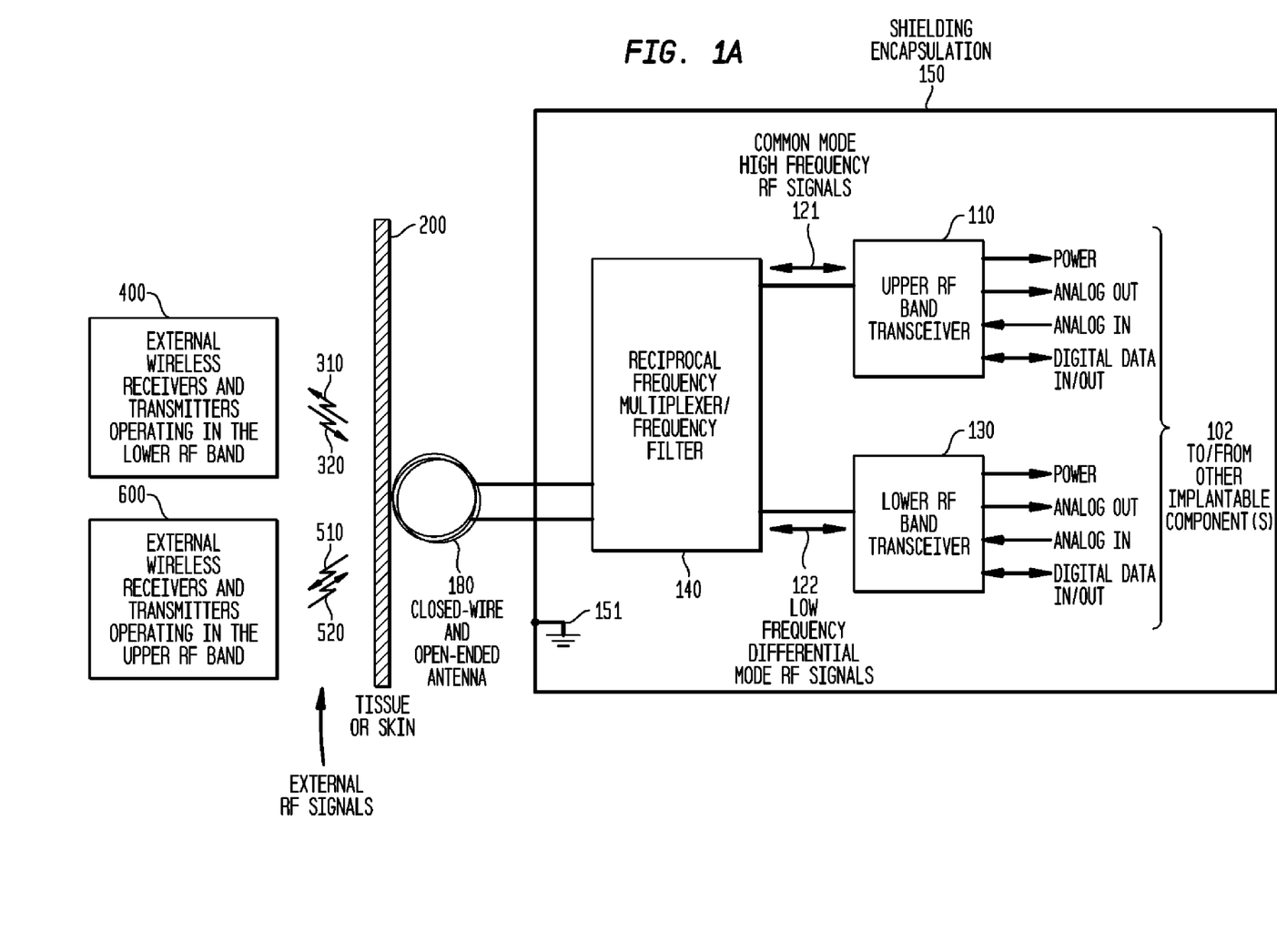
FIG. 1A is a schematic block diagram of an implantable medical device according to one embodiment of the present invention.

FIG. 1A is a schematic block diagram of an active implantable medical device according to one embodiment of the present invention. Active implantable medical device (AIMD) 100 comprises a single implantable antenna 180. Antenna 180 is physically formed, in this illustrative embodiment, by a closed electrical loop with one or multiple windings. Such an antenna is referred to herein as a closed-wire antenna. As one of ordinary skill in the art will find apparent from the description herein, antenna 180 has both the properties of a closed-wire loop antenna and of an open-ended wire antenna. Antenna 180 is located outside of a shielding encapsulation 150 of AIMD 100, and is implanted beneath skin 200 of a patient or recipient.

To perform its dual band role, antenna 180 is connected to a reciprocal frequency multiplexer/frequency filter 140. Antenna 180 operates furthermore in combination with a ground plane 151 which, in the illustrative embodiment, is integrated into shielding encapsulation 150. AIMD 100 further comprises an open-ended antenna matching unit 120 (FIG. 3), an upper band transceiver 110 and lower band transceiver 130, each of which are described in detail below. As is well-known to those of ordinary skill in the relevant art, a transceiver comprises a receiver and transmitter, and processes radio frequency signals that are received and/or that are to be transmitted. Transceivers 110 and 130 may be provided with inputs and outputs for receiving and transmitting analog and/or digital data and power signals to the other implanted components of AIMD 100. As one of ordinary skill in the art would appreciate, in alternative embodiments, either one or both transceivers 110, 130 are solely a receiver and/or solely a transmitter.

For communicating a relatively high-frequency RF signal over an upper RF band, antenna 180 behaves as a monopole element with an asymmetrical RF power hot-feed point at both coil ends and a feeder ground attached to ground plane 151. As noted, in this embodiment, ground plane 151 is the electrical shielding of implant encapsulation 150. In an alternative embodiment, ground plane 151 may be any printed circuit board (PCB) ground. This may be implemented, for example, when implant encapsulation 150 is unshielded. As one of ordinary skill in the relevant art will find apparent from the, matching unit 120 is configured to place antenna 180 for the upper RF band into resonance and optimum impedance. This is described in further detail below.

For communication over the lower RF band, antenna 160 behaves as a closed-wire loop, preferably with a symmetrical feed point. Current from lower RF band transmitter 130 through antenna 160 generates a magnetic field. This magnetic field is set up in accordance with the Biot-Savart law, which describes magnetic field set up due to a steady flowing line current in a current wire element or steady current density (magneto-statics). The signal applied to lower RF band receiver 130 is a voltage induced in the loops of antenna 180 that is proportional to the change of magnetic flux. As one of ordinary skill in the art would appreciate, this is based on Faraday's law.

Circuit 140 comprises a filter (not shown in FIG. 1) for the upper radio frequency band. In one embodiment, this filter is a high-pass filter. In an alternative embodiment, this filter is a band-pass filter. Other embodiments are contemplated. Circuit 140 also comprises a filter for the lower radio frequency band. This filter is a low-pass filter in one embodiment of the present invention. In an alternative embodiment, this filter is also a band-pass filter. Other embodiments of this filter are contemplated as well.

Reciprocal frequency multiplexer/filter circuit 140 is configured to concurrently frequency-filter high- and low-frequency external RF signals received by said implantable antenna, and to concurrently frequency-multiplex common-mode high-frequency RF signals and differential-mode low-frequency RF signals to form high- and low-frequency external RF signals, respectively, for transmission to said one or more external devices via said internal antenna 180, said common-mode high- and differential-mode low-frequency RF signals corresponding to said internal signals generated by said implantable component.

Figure 1B:
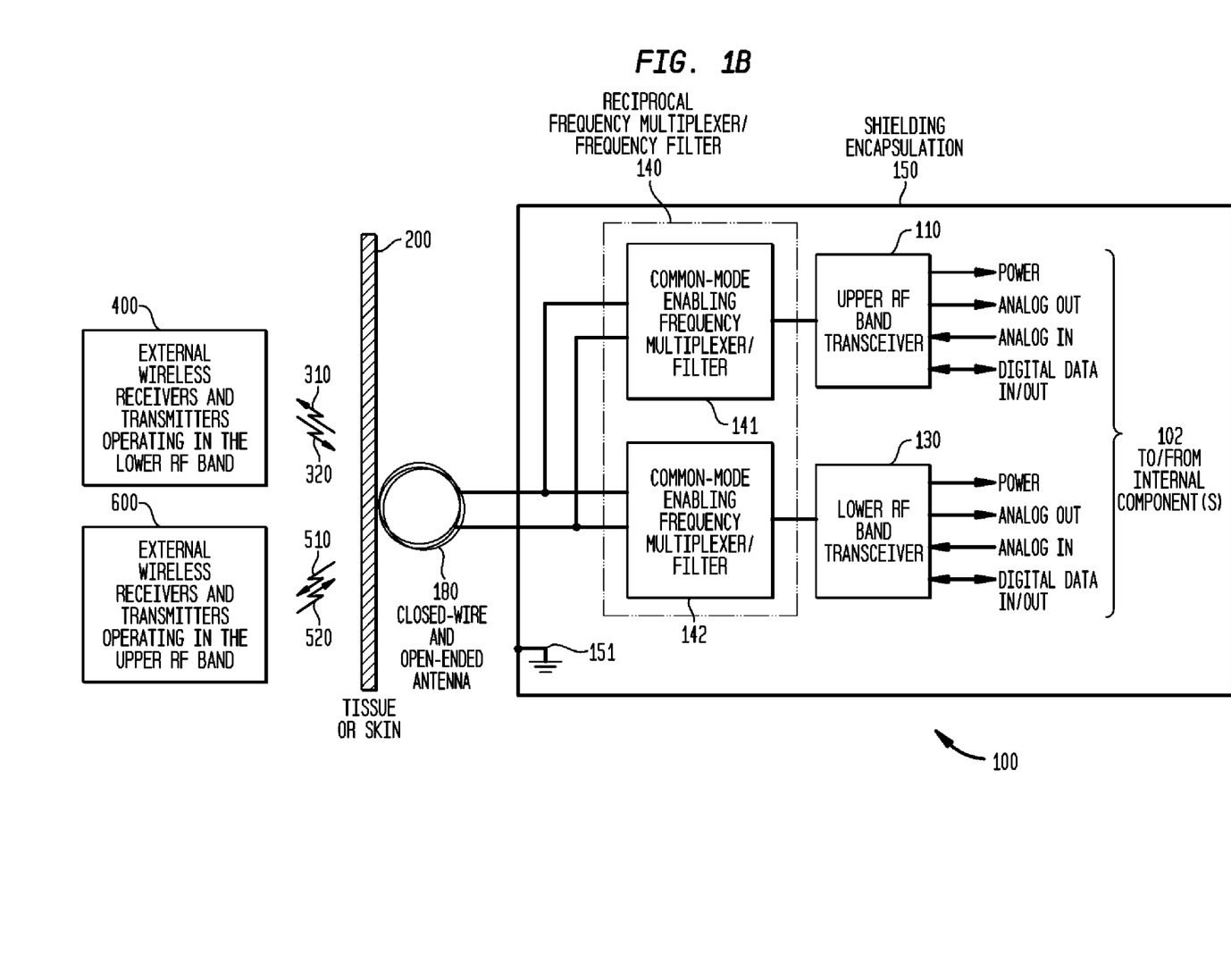
FIG. 1B is a more detailed schematic block diagram of the implantable medical device illustrated in FIG. 1A.

As shown in FIG. 1B, circuit 140 comprises a common-mode enabling frequency multiplexer/filter circuit configured to filter said high-frequency external RF signals received by said implantable antenna so as to pass only said common-mode high-frequency RF signals for processing to generate one or more of said internal signals, and to multiplex common-mode high frequency RF signals corresponding to said internal signals received from said implantable component to form a high-frequency external RF signal for transmission to the one or more external devices via said implantable antenna; and a differential-mode enabling frequency multiplexer/filter circuit configured to filter said low-frequency external RF signals received by said implantable antenna so as to pass only said differential-mode low-frequency RF signals for processing to generate one or more of said internal signals, and to multiplex differential-mode low-frequency RF signals corresponding to one or more of said internal signals received from said implantable component to form a low-frequency external RF signal for transmission to the one or more external devices via said implantable antenna.

Figure 2:
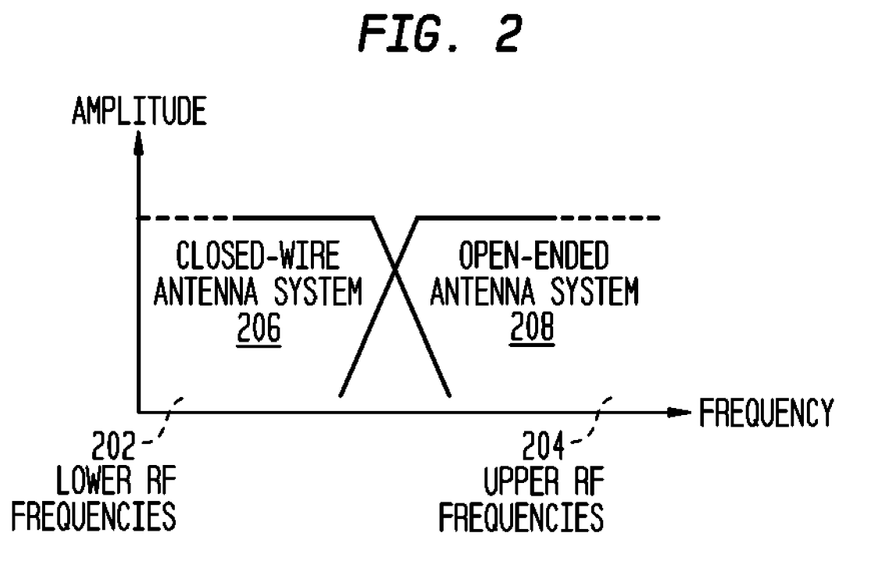
FIG. 2 is an amplitude versus frequency graph representing the low-pass and high-pass characteristics of the band diplexer illustrated in FIG. 1, in accordance with one embodiment of the present invention.

FIG. 2 is an amplitude versus frequency graph illustrating the relationship between the lower RF frequencies 202 and upper RF frequencies 204. As shown in FIG. 2, lower RF frequencies are transmitted and/or received via closed-wire antenna system 206 while upper RF frequencies 204 are transmitted and/or received by open-ended antenna system 208.

The resulting separation or isolation between lower RF frequency signals; that is, the lower RF band 202, and the high RF frequency signals; that is, the upper RF band 204, allows for simultaneous operation over both frequency bands. Signals transmitted over upper RF band communication link 510 from upper RF band transmitter 110 to external devices 600 will not interfere with signals transmitted over lower RF band communication link 320 from external devices 400 towards lower RF band receiver 130. Transmitted signals 310 from the lower RF band transmitter 130 towards external devices 400 will not interfere with upper RF band signals 520 from external devices 600 towards upper RF band receiver 110.

Figure 3:
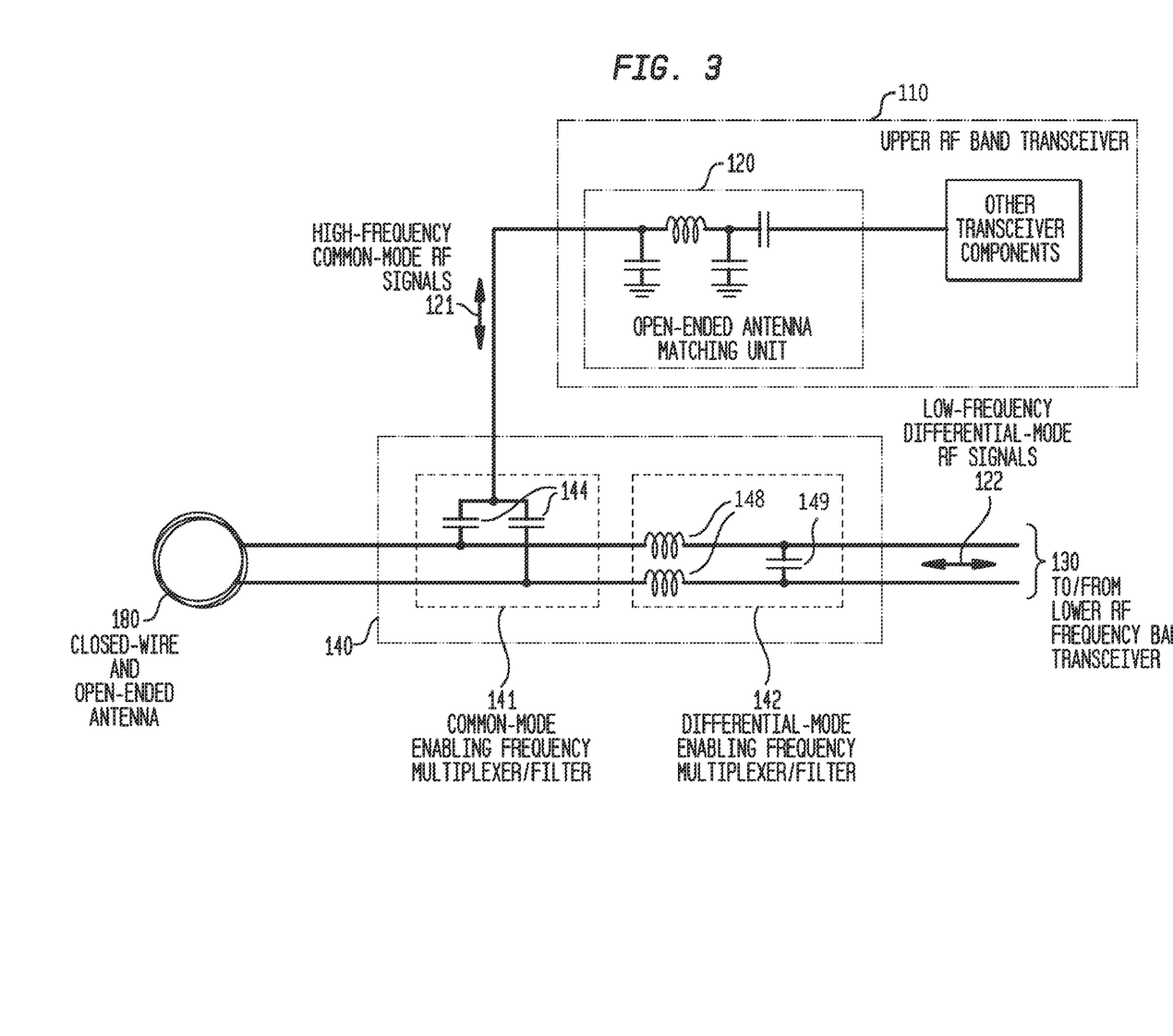
FIG. 3 is a schematic block diagram of the implantable medical device illustrated in FIGS. 1A and 1B, depicting exemplary embodiments of the reciprocal frequency multiplexer/filter and an open-ended antenna matching circuit for the implantable antenna, in accordance with one embodiment of the invention.

FIG. 3 is a schematic diagram of one embodiment of the active implantable medical device illustrated in FIGS. 1A and 1B. Referring to FIG. 3, common-mode enabling frequency multiplexer/filter circuit 141 comprises high-frequency or upper RF band coupling elements which filter the lower RF signals for upper RF transceiver system 110. The embodiment of this circuit 141 illustrated in FIG. 3 is comprised of two low-valued capacitors 144. As one of ordinary skill in the art would appreciate, circuit 141 may contain other circuit elements in addition to or in place of capacitors 144 in alternative embodiments of the present invention. It should also be appreciated that the specific values of capacitors 144 may be selected by one of ordinary skill in the art to filter a specific range of lower frequency RF signals.

Circuit 140 also comprises low-frequency or lower RF band coupling elements 142 which filter or block high-frequency RF signals for lower RF transceiver system 130. The embodiment of this circuit 142 illustrated in FIG. 3 is comprised of two low-valued inductors 148. As one of ordinary skill in the art would appreciate, circuit 142 may contain other circuit elements in addition to or in place of inductors 148 in alternative embodiments of the present invention. For example, optionally, a capacitor 149 may be included in circuit 142 to obtain resonance at the lower RF band for improving power and data transfer efficiency. It should also be appreciated that the specific values of inductors 148 and capacitor 149 may be selected by one of ordinary skill in the art to filter a specific range of upper frequency RF signals.

Implementing circuit 140 provides for common-mode and differential-mode operations, resulting in high-frequency common-mode RF signals 121 and low-frequency differential-mode RF signals 122. Differential mode is used for the closed-wire antenna system in the lower RF band, whereas common mode is used for the open-ended antenna system in the upper RF band. Because of the different modes of operation, additional electrical isolation between the two transceiver systems 110 and 130 may be obtained.

The low-frequency communication link; that is, the RF signals transmitted and received over lower RF band 310, 320, are based on magnetic induction and is preferably below approximately 30 MHz, and more preferably below approximately 25 MHz, and even more preferably below approximately 15 MHz. Such a low-frequency communication link utilizes the non-propagating quasi-static magnetic field, as described above. As is well-known in the art, the magnetic field exhibits very high roll-off behaviour as a function of distance.

The high-frequency communication link; that is, the high-frequency external RF signals transmitted and received over upper RF band 510/520 are based on electromagnetic field propagation, and is preferably higher than 30 MHz, more preferably much higher than 50 MHz. In one embodiment, such high-frequency RF signals are higher than 100 MHz. The power of a plane wave in the far-field rolls off as one over the distance from the source squared.

Medical implant device 100 is able to communicate wirelessly with other devices over an upper RF band and a lower RF band, simultaneously or consecutively in time. The communication link over the lower RF band is a magnetic induction link, operating in the reactive near-field. The communication link over the upper RF band may operate in the reactive near-field, the radiating near-field and/or in the propagating far-field. Operation in the reactive near-field necessitates that the antennas of the implant and the communicating device be arranged in close proximity.

A power transfer from external devices 400 and 600, operating in the reactive near-field at respectively lower RF bands and upper RF bands towards the AIMD 100, over the lower RF band 320 or upper RF band 520, can be established with a coil antenna 180 connected to reciprocal frequency multiplexer/filter 140, in combination with a ground plane 151 for the upper RF band, an open-ended antenna-matching unit 120, an upper band transceiver 110 and a lower band transceiver 130.

In the reactive near-field, where coils are magnetically closely coupled, the external device 400 could transfer sufficient power over the lower frequency band 320 towards the AIMD to provide the implant with electrical energy enabling operation or charging of its implanted battery if present.

Figure 4:
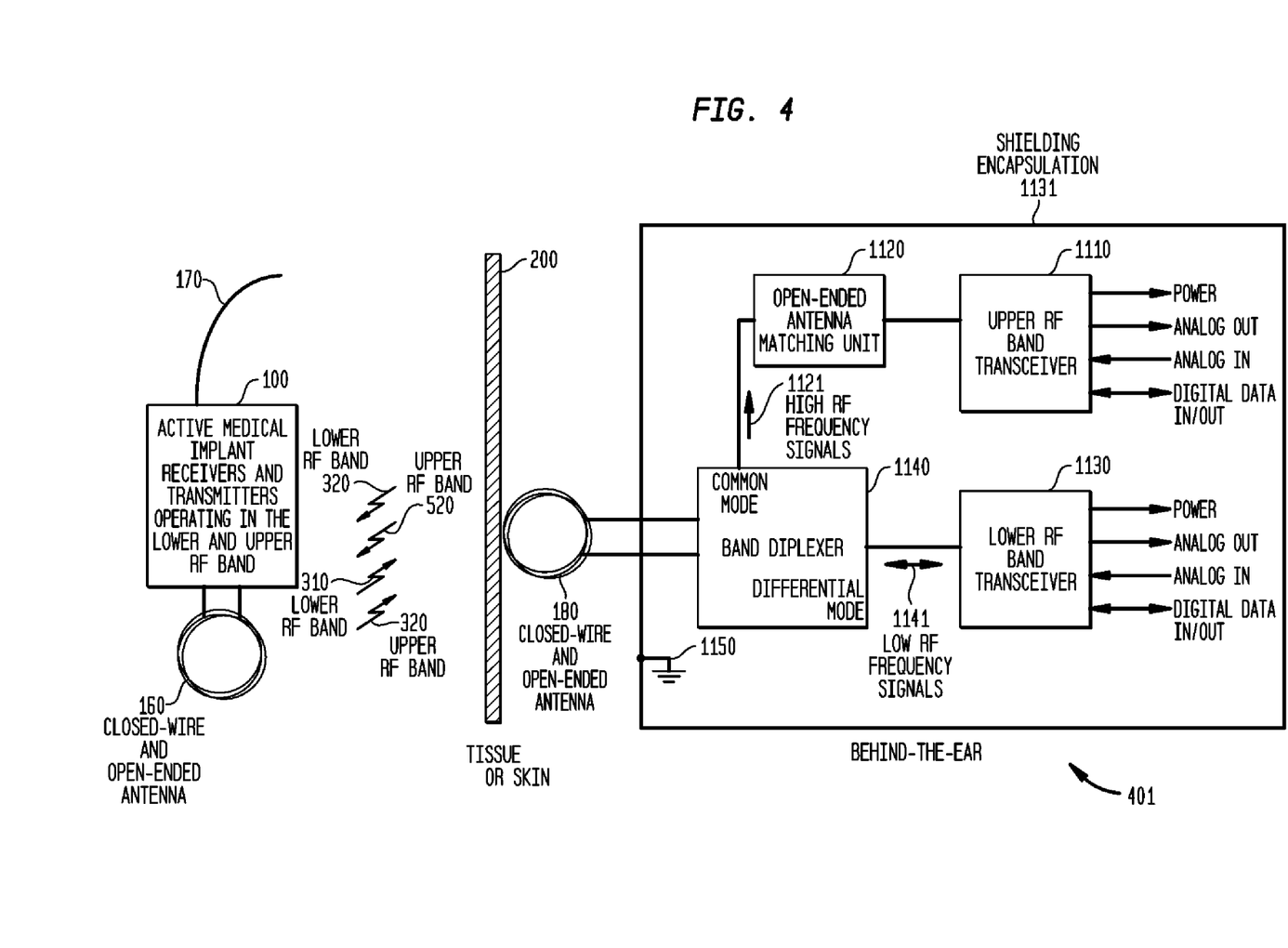
FIG. 4 is a schematic block diagram of the implantable medical device, in accordance with an alternative embodiment of the present invention.

Referring to FIG. 4, in another aspect of the invention, an AIMD 401 may communicate with an external device 100 over a first, lower radio-frequency band and/or a second, upper radio frequency band. In this illustrative embodiment, the communication link between implant device 401 and external device 100 over lower RF band (310, 320) is based on magnetic induction. In one example, lower RF band communication link 310/320 utilizes the non-propagating quasi-static magnetic field (reactive near-field). Similarly, in one example, communication link 510 and 520 over the upper RF band operates in the near-field and/or in the propagating far-field (electromagnetic field propagation).

FIG. 4 shows an antenna 180 for an external device 401 (e.g. a behind-the-ear device), physically formed by a closed electrical loop with one or multiple windings. Antenna 180 has the properties of both a closed-wire loop antenna and an open-ended wire antenna. In this embodiment, circuit 140 is implemented as a band diplexer 1140. Antenna 180 operates furthermore in combination with a ground plane 1150, an open-ended antenna matching unit 1120, an upper band transceiver 1110 and lower band transceiver 1130. As noted above, such a ground plane can be the electrical shielding of the encapsulation of external device 401 or a printed circuit board ground. The configuration of band diplexer 1140 and antenna matching unit 1120 may be similar to that of circuit 140 and antenna matching unit 120 of implant 100. Hence, band diplexer 1140 may comprise a filter for the lower RF band signals (differential mode signals) and a filter for the upper RF band signals (common mode signals).

Antenna 180 allows for the establishment of bidirectional data communication links over a first, lower radio frequency band (310, 320) and over a second, upper radio frequency band (510, 520). The two bands may be used simultaneously or consecutively in time for bidirectional communication between external device 401 and the AIMD 100 or other devices. In order to use the lower RF band magnetic induction link, antenna 160 of the external device may be located at short range of internal antenna 100. Lower RF band transceiver 1130 may be a transmitter or receiver only. Similarly, upper RF band transceiver 1110 may be a transmitter or receiver only.

Figure 5:
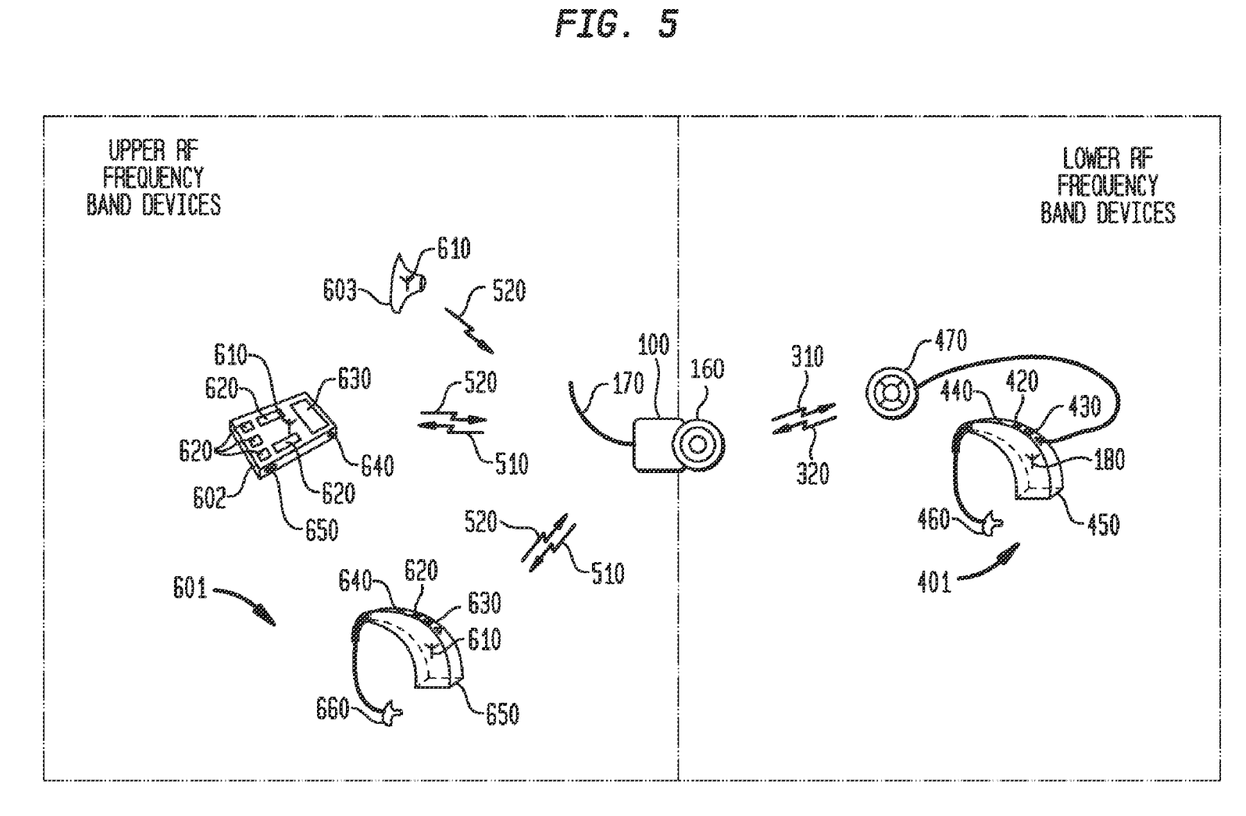
FIG. 5 is a simplified perspective view of a cochlear implant comprising an active implantable medical device (AIMD) and external devices, in accordance with an embodiment of the present invention.

FIG. 5 illustrates an embodiment of the AIMD of the invention as a cochlear implant 100 in a hearing prosthesis. Cochlear implant 100 is an implantable device comprising a cochlea stimulating electrode 170 that stimulates by applying electrical signals the auditory nerves of the cochlea or brainstem. Depending on cause of recipient's deafness, a mechanical implantable actuator stimulating middle or inner parts of the ear can be placed in conjunction or as alternative. The cochlear implant is implanted beneath the human skin, near the left or right ear. The cochlear implant comprises a combined open-ended and closed-wire antenna 160, and an implantable battery (not shown). The implant communicates with several external devices (401, 601, 602, 603) as summed hereafter.

A first type of external device is behind-the-ear (BTE) device 401, which comprises a dual-band coil antenna 180 according to the one of FIG. 4. Antenna 180 is a combined open-ended and closed-wire antenna similar to the principle of the combined coil antenna of an implant. BTE device 401 allows wireless bidirectional data transfer (310, 320) over the lower RF band. Therefore, either coil antenna 180 or headpiece 470 may be used. Coil antenna 180 creates a magnetic induction link with the dual-band coil antenna 160 of the implant. Headpiece 470 is a coil antenna, which may be connected externally to the BTE device 401. This allows the attachment of headpiece 470 in close proximity to the combined coil antenna 160 of the implant device 100. Attachment or fixation between headpiece 470 and antenna coil 160 of the implant may be done by a permanent magnet. Headpiece 470 is particularly useful for wireless transcutaneous power transfer over the lower frequency band 320.

The behind-the-ear device 401 may further comprise a microphone system 440, human interface controls and buttons 420, a small display 430, in-the-ear speaker 460, digital and analogue inputs and outputs 450, signal processing circuits, memory and batteries.

A second type of behind-the-ear device 601 is capable of communicating wirelessly over an upper RF band. The bidirectional data transfer over that upper RF band uses electromagnetic field propagation (510, 520). Therefore, BTE device 601 comprises an open-ended antenna 610, e.g. of monopole or dipole type. BTE device 601 may further comprise a microphone system 640, human interface controls and buttons 620, a small display 630, an in-the-ear speaker 660, digital and analog inputs and outputs 650, signal processing circuits, memory and batteries. BTE device 401 may equally well act as BTE device 601, as it comprises a dual band antenna 180 of the invention.

Another type of external device is a remote control or handheld device 602, which incorporates a receiver and transmitter system with antenna 610 for bidirectional wireless communication (510, 520) in the upper RF band. The remote control 602 may comprise a microphone system 640, human interface controls and buttons 620, a display 630, digital and analogue inputs and outputs 650, signal processing circuits, memory and batteries.

An additional type of external device is an in-the-ear device 603, comprising a transmitter system with antenna 610 for unidirectional wireless communication 520 in the upper RF band. The in-the-ear device 603 may comprise a microphone system, human interface controls and buttons, signal processing circuits, memory and batteries.

The radiating elements (antennas) 610 of the second type of behind-the-ear device 601, the remote control 602 and in-the-ear device 603 are open-ended wire antennas such as monopole, stub, helix or helical wound coil, meander or dipole antennas. In case of a dipole antenna, no ground plane is needed.

Figure 6:
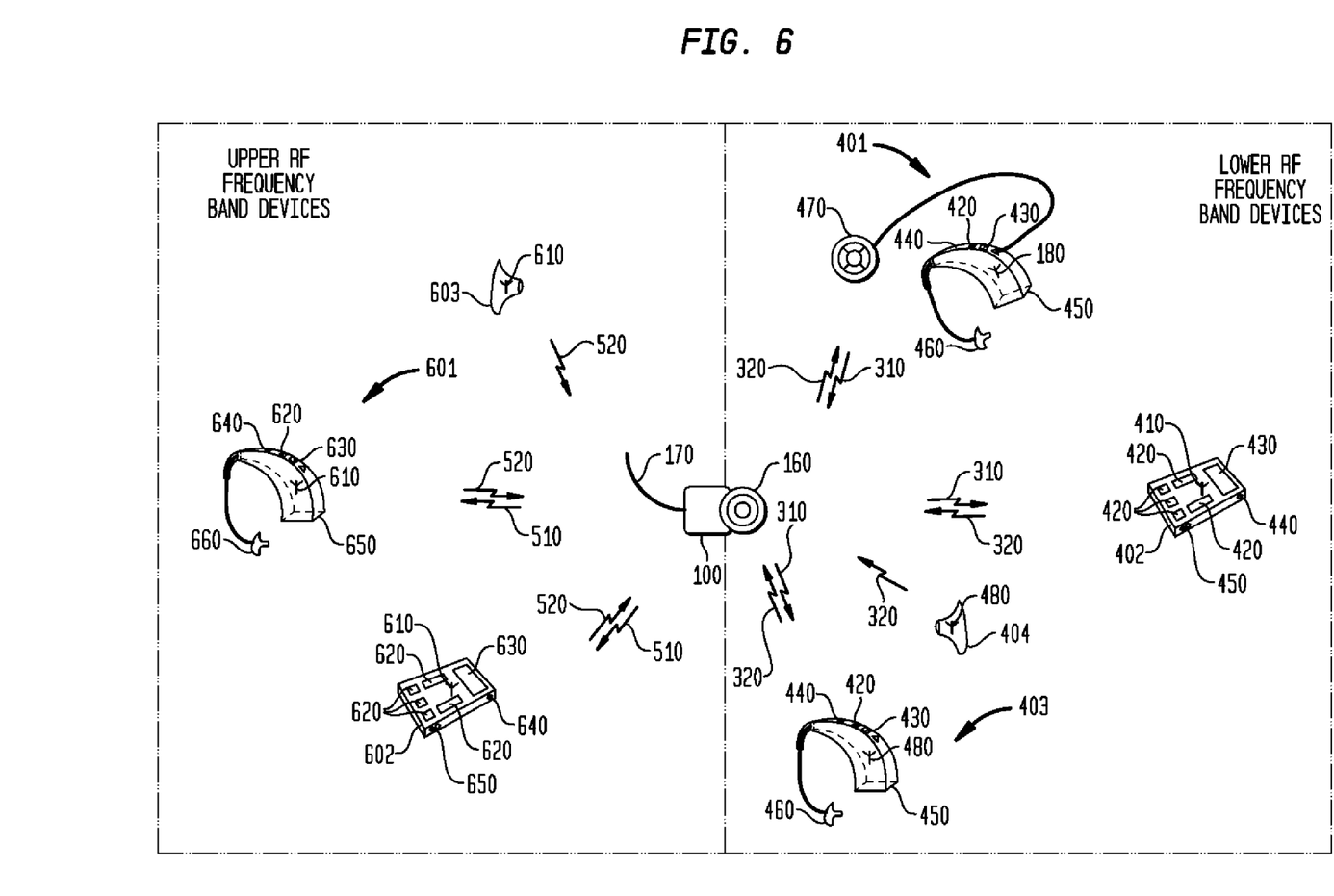
FIG. 6 is a simplified perspective view of a cochlear implant comprising an active implantable medical device (AIMD) and external devices, in accordance with an alternative embodiment of the present invention.

FIG. 6 illustrates other system combinations. A remote control 402, a BTE device 403 and an in-the-ear device 404 may communicate uni- or bi-directionally with implant 100 over a lower RF band by using a coil antenna 480 to create a magnetic induction link with the dual-band coil antenna 160 of the implant. Therefore, remote control 402, BTE device 403 and in-the-ear device 404 each comprise a closed-wire antenna 480 for wireless communication over a lower RF band.

Since the implant can operate simultaneously in the lower and upper RF bands by implementation of two transceivers, bilateral or binaural communication between two BTEs or even two implants is supported in one RF band, whilst having a supplementary communication link in the other RF band. External devices 401, 402, 403 and 404 may also communicate with each other via the lower RF link. External devices 601, 602, 603 may communicate with each other via the upper RF link. A remote unit 402 or 602 may communicate with the implant 100 via a BTE device 401 or respectively 403 or 601. Bilateral communication comprises telemetry, control data, signalling data and audio streaming.

The wireless communication links of the present invention may be used for controlling and programming medical implant devices. The two-band communication capabilities of the implant devices of this embodiment of the invention facilitate energy optimization. Battery cells supply implant devices with power, providing the recipient with limited duration autonomy. Since recipients and the market demand for longer system autonomy and miniaturization, an optimized design of the wireless communication link with very low power consumption is required.

According to an additional aspect of the invention, a method of wireless communication is provided between any AIMD of the invention and an external device, such as a remote control unit or a remote programmable unit. Embodiments of the present method allow to reduce energy consumption of the AIMD. According to the method, the forward wireless communication from the external device to the AIMD operates over the lower band magnetic induction link (near-field communication) and the backward wireless communication from the AIMD to the external device operates over the upper band electromagnetic field propagation link (far-field communication). Over a long range, an EM-field wireless communication uses a lower amount of energy resources than an MI field wireless communication. Hence, the method allows for a reduction in power consumption of the AIMD of the invention.

Furthermore, in case that the forward communication takes place over the magnetic induction link only, an upper RF band receiver is not required on the AIMD. In case that the backward communication takes place over the electromagnetic field propagation link only, a magnetic induction transmitter is not required on the AIMD. This facilitates the reduction in size of the AIMD.

According to a further aspect of the invention, a method of wireless communication is provided between a fitting system and a hearing aid system. Since recipients of hearing aid systems have different auditory defects, each hearing aid device must be adjusted, "fitted" or "mapped" specifically to an individual's needs and his/her responses to sound. This fitting process requires an initial appointment with an audiologist at a clinical implant center. The fitting process adjusts the "map" as the brain adapts to incoming sound. Wireless fitting or mapping offers benefit to the audiologist and to the recipients, especially when the recipient is a child. The method of the invention optimizes the power consumption at recipient's side during fitting sessions by selecting a dedicated wireless technology for forward link and another dedicated wireless technology for back-data link.

The fitting system generally is a remote, external programmable unit, such as a PC, provided with a wireless communication link with the recipient's hearing aid system. The remote programmable unit can easily increase the magnetic field presented to the target devices (BTE device or cochlear implant). This reduces amplification and power consumption for the target (hearing aid) device. By way of example, the remote programming unit (RPU) is capable of supplying more power to its MI transmitter because the RPU is connected to the mains (electrical wired power distribution 110 Vac/230 Vac) and hence has the availability of quasi unlimited power. The power consumption of the transceiver of the hearing aid system (e.g. transceiver 1110) hence can be made much lower than the power consumption of the transceiver of the fitting or RPU system. Moreover, due to the increased magnetic field, the target device need not be equipped with a highly selective receiving filter for the MI receiver, because a third party's MI interference field is strongly attenuated (inversely proportional to $r^3$). This saves space on the target device (BTE device, cochlear implant).

A further reduction in power consumption of the target device may be attained in certain embodiments—the hearing aid device (e.g. a BTE device or a cochlear implant)—may be obtained by having the forward wireless communication link from the fitting system to the device established through magnetic induction (near-field communication) and the backward wireless communication link from the device to the fitting system established through electromagnetic field propagation (far-field communication). Moreover, in case the far-field communication is always established unidirectionally (i.e. backward), a far-field receiver and selective receiving filter may be absent on the hearing aid device. This facilitates the saving of space on the BTE device or the cochlear implant.

Embodiments of the present invention may equally be applied more in general to BTE devices. In the case of wireless communication between a BTE device and a second external device, such as a remote control unit or a remote programmable unit, the forward wireless communication from the second external device to the BTE device operates over the lower band magnetic induction link (near-field communication) and the backward wireless communication from the BTE device to the second external device operates over the upper band electromagnetic field propagation link (far-field communication). Hence, embodiments of the method also allow for the reduction of power consumption of the BTE device.

Furthermore, in case that forward communication takes place over the magnetic induction link only, an upper RF band receiver is not required on the BTE device. In case that backward communication takes place over the electromagnetic field propagation link only, a magnetic induction transmitter is not required on the BTE device.

As one of ordinary skill in the art would appreciate from the foregoing, there are a variety of benefits provided by different embodiments of the present invention, including, for example, using a single antenna to simultaneously transmit/receive RF signals at different frequencies while maintaining electrical RF isolation between transceiver ports due to common-mode and differential-mode operations. This enables, for example, for an implanted battery to be charged over the lower RF band simultaneously in time with a bidirectional communication link in the upper RF band. As another example, coexistence and simultaneous operation between the existing 5 MHz power/data link and any other wireless external devices is possible.

It is noted that certain embodiments of circuit 140, including the band diplexer described above, contain physical small surface mount (SMT) elements, since in certain embodiments the capacitor and inductance values are very small, e.g. 10 pF and 100 nH for lumped elements.

Magnetic induction technology is most optimized for power transfer towards the implant and bidirectional communication links ranging, in one example 30 cm or shorter, whereas electromagnetic bidirectional communication links reaches ranges of several meters or more.

As one of ordinary skill in the art would appreciate, which provide improved or at least alternative wireless communication possibilities compared to prior art devices and wireless communication methods. Active implantable medical devices envisaged by the present invention include, but are not limited to, cochlear implants, nerve stimulators, pace makers, glucose meters, and any other type of active implantable medical device requiring wireless communication.

Further features and advantages of the present invention may be found in U.S. Provisional Application No. 60/924,807, entitled "IMPLANTABLE MEDICAL DEVICE WITH INTEGRATED ANTENNA SYSTEM," and filed on May 31, 2007, and U.S. Provisional Application No. 60/924,800, entitled "HEARING AID DEVICE WITH ANTENNA," and filed on May 31, 2007 which are hereby incorporated by reference herein.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device having an implantable component configured to at least one of receive external data, generate internal data, and receive power signals, the device comprising:
   an implantable antenna for transmitting and receiving external radio frequency (RF) signals to and from one or more devices positionable external a patient's body; and
   a reciprocal frequency multiplexer-filter circuit configured to concurrently frequency-filter high- and low-frequency external RF signals received by said implantable antenna, and to concurrently frequency-multiplex common-mode high-frequency RF signals and differential-mode low-frequency RF signals to form high- and low-frequency external RF signals, respectively, for transmission to said one or more external devices via said implantable antenna, said common-mode high- and differential-mode low-frequency RF signals corresponding to said internal data generated by said implantable component.

2. The implantable medical device of claim 1, wherein said circuit comprises:
   a common-mode enabling frequency multiplexer-filter circuit configured to filter said high-frequency external RF signals received by said implantable antenna so as to pass only said common-mode high-frequency RF signals for processing to generate first instances of said internal data, and to multiplex common-mode high frequency RF signals corresponding to said first instances of said internal data received from said implantable component to form a high-frequency external RF signal for transmission to the one or more external devices via said implantable antenna; and
   a differential-mode enabling frequency multiplexer-filter circuit configured to filter said low-frequency external RF signals received by said implantable antenna so as to pass only said differential-mode low-frequency RF signals for processing to generate second instances of said internal data, and to multiplex differential-mode low-frequency RF signals corresponding to said second instances of said internal data received from said implantable component to form a low-frequency external RF signal for transmission to the one or more external devices via said implantable antenna.

3. The medical device of claim 1, wherein said implantable antenna comprises:
   one or more windings.

4. The medical device of claim 1, wherein said low-frequency external RF signals comprise:
   a magnetoinductive (MI) near-field signal.

5. The medical device of claim 1, wherein said low-frequency external RF signals comprise:
   a reactive near-field signal.

6. The medical device of claim 1, wherein said high-frequency external RF signals comprise:
   a radiating near-field signal.

7. The medical device of claim 1, wherein said high-frequency external RF signals comprise:
   an electromagnetic (EM) far-field signal.

8. The medical device of claim 1, further comprising:
   a lower RF band transceiver, connected to said circuit, configured to process said low-frequency differential-mode RF signals generated by said circuit into one or more of said internal data, and vice-versa; and
   an upper RF band transceiver, connected to said circuit, configured to process said high-frequency differential-mode RF signals generated by said circuit into one or more of said internal data, and vice-versa.

9. The medical device of claim 8, wherein:
   said implantable component includes other components; and
   said transceivers are each configured to unidirectionally transfer power from said implantable antenna to said other components using a reactive near field.

10. The medical device of claim 1, wherein the frequency of said low-frequency external RF signals are below or equal to approximately 40 MHz.

11. The medical device of claim 10, wherein the frequency of said low-frequency external RF signals are below or equal to approximately 30 MHz.

12. The medical device of claim 11, wherein the frequency of said low-frequency external RF signals are below or equal to approximately 25 MHz.

13. The medical device of claim 1, wherein the frequency of said high-frequency external RF signals are above or equal to approximately 20 MHz.

14. The medical device of claim 13, wherein the frequency of said high-frequency external RF signals are above or equal to approximately 30 MHz.

15. The medical device of claim 14, wherein the frequency of said high-frequency external RF signals are above or equal to approximately 50 MHz.

16. The medical device of claim 15, wherein the frequency of said high-frequency external RF signals are above or equal to approximately 100 MHz.

17. The medical device of claim 1, further comprising:
   an antenna matching unit, operationally coupled to said circuit, configured to match impedance of said implantable antenna to an open-ended antenna for transmitting and receiving said high-frequency external RF signals.

18. The medical device of claim 1, wherein one or more of said high- and low-frequency external RF signals comprises a data signal from the group consisting of:
   telemetry data signal;
   control data signal;
   signalling data signal; and
   audio streaming data signal.

19. The medical device of claim 1, wherein said medical device comprises:
   a cochlear implant.

20. The medical device of claim 1, wherein said implantable antenna has properties of both:
   a closed-wire antenna; and
   an open-ended antenna.

21. A cochlear implant comprising:
   one or more external devices comprising an external sound processor unit to be worn on the body of a recipient; and
   an implantable medical device having an implantable component configured to at least one of receive external data, generate internal data, and receive power signals, comprising:
   an implantable antenna for transmitting and receiving external radio frequency (RF) signals to and from one or more devices positionable external a patient's body; and
   a reciprocal frequency multiplexer-filter circuit configured to concurrently frequency-filter high- and low-frequency external RF signals received by said implantable antenna, and to concurrently frequency-multiplex common-mode high-frequency RF signals and differential-mode low-frequency RF signals to form high- and low-frequency external RF signals, respectively, for transmission to said one or more external devices via said implantable antenna, said common-mode high- and differential-mode low-frequency RF signals corresponding to said internal data generated by said implantable component.

22. The cochlear implant of claim 21, wherein said circuit comprises:
   a common-mode enabling frequency multiplexer-filter circuit configured to filter said high-frequency external RF signals received by said implantable antenna so as to pass only said common-mode high-frequency RF signals for processing to generate first instances of said internal data, and to multiplex common-mode high frequency RF signals corresponding to said first instances of said internal data received from said implantable component to form a high-frequency external RF signal for transmission to the one or more external devices via said implantable antenna; and
   a differential-mode enabling frequency multiplexer-filter circuit configured to filter said low-frequency external RF signals received by said implantable antenna so as to pass only said differential-mode low-frequency RF signals for processing to generate one or more of said internal data, and to multiplex differential-mode low-frequency RF signals corresponding to said second instances of said internal data received from said implantable component to form a low-frequency external RF signal for transmission to the one or more external devices via said implantable antenna.

23. The cochlear implant of claim 21, wherein said implantable antenna comprises:
   one or more windings.

24. The cochlear implant of claim 21, wherein said low-frequency external RF signals comprise:
   a magnetoinductive (MI) near-field signal.

25. The cochlear implant of claim 21, wherein said low-frequency external RF signals comprise:
   a reactive near-field signal.

26. The cochlear implant of claim 21, wherein said high-frequency external RF signals comprise:
   a radiating near-field signal.

27. The cochlear implant of claim 21, wherein said high-frequency external RF signals comprise:
   an electromagnetic (EM) far-field signal.

28. The cochlear implant of claim 21, further comprising:
   a lower RF band transceiver, connected to said circuit, configured to process said low-frequency differential-mode RF signals generated by said circuit into one or more of said internal data; and
   an upper RF band transceiver, connected to said circuit, configured to process said high-frequency differential-mode RF signals generated by said circuit into one or more of said internal data.

29. The cochlear implant of claim 28, wherein:
   said implantable component includes other components; and
   said transceivers are each configured to unidirectionally transfer power from said implantable antenna to components of the medical device using a reactive near field.

30. The cochlear implant of claim 21, wherein the frequency of said low-frequency external RF signals are below or equal to approximately 40 MHz.

31. The cochlear implant of claim 30, wherein the frequency of said low-frequency external RF signals are below or equal to approximately 30 MHz.

32. The cochlear implant of claim 31, wherein the frequency of said low-frequency external RF signals are below or equal to approximately 25 MHz.

33. The cochlear implant of claim 21, wherein the frequency of said high-frequency external RF signals are above or equal to approximately 20 MHz.

34. The cochlear implant of claim 33, wherein the frequency of said high-frequency external RF signals are above or equal to approximately 30 MHz.

35. The cochlear implant of claim 34, wherein the frequency of said high-frequency external RF signals are above or equal to approximately 50 MHz.

36. The cochlear implant of claim 35, wherein the frequency of said high-frequency external RF signals are above or equal to approximately 100 MHz.

37. The cochlear implant of claim 21, further comprising:
   an antenna matching unit, operationally coupled to said circuit, configured to match impedance of said implantable antenna to an open-ended antenna for transmitting and receiving said high-frequency external RF signals.

38. The cochlear implant of claim 21, wherein one or more of said high-frequency external RF signals and low-frequency external RF signals comprises a data signal from the group consisting of:
   telemetry data signal;
   control data signal;
   signalling data signal; and
   audio streaming data signal.

39. The cochlear implant of claim 21, wherein said implantable antenna has properties of both:
   a closed-wire antenna; and
   an open-ended antenna.

40. The cochlear implant of claim 21, wherein said external sound processor unit comprises:
   a behind-the-ear (BTE) sound processor unit.

41. The cochlear implant of claim 40, wherein said BTE sound processor unit comprises:
   a connector for a closed-wire antenna external to said BTE sound processor unit for transcutaneously transferring power to said implantable components of the cochlear implant.

42. The cochlear implant of claim 40, wherein said one or more external devices further comprises:
   a device configured to be located in-the-ear canal of the recipient.

43. The cochlear implant of claim 40, wherein at least one of said one or more external devices
   can be at least one of a remote control device and a hand-held device.

44. A method of bidirectional wireless communication between an implantable medical device and an external device comprising:
  concurrently and multiplexedly communicating including:
    communicating unidirectionally from the external device to the implantable medical device over a first wireless link in a first RF band in the MI near-field using differential-mode signalling; and
    communicating unidirectionally from the implantable medical device to the external device over a second wireless link in a second RF band in the EM-field using common-mode signalling.

45. The method of claim 44, wherein the second RF band is in the EM far field.

46. The method of claim 44, wherein said second RF band is higher in frequency than said first RF band.

47. The method of claim 44, wherein an upper end of the second RF band is below or equal to approximately 40 MHz.

48. A hearing prosthesis comprising:
  an internal antenna for transmitting and receiving RF signals to and from one or more external devices; and
  a band diplexer, connected to the internal antenna, comprising: a first filter configured to filter for a differential-mode first signal to be at least one of transmitted and received in a first RF band, and a second filter configured to filter for a common-mode second signal to be at least one of transmitted and received in a second RF band, wherein the common-mode second RF band is higher in frequency than the differential-mode first RF band, the diplexer being configured to operate the first and second filters concurrently.

49. The hearing prosthesis of claim 48, wherein the antenna comprises one or multiple windings.

50. The hearing prosthesis of claim 48, wherein the antenna is arranged to at least one of transmit and receive the first signal over an MI near-field and arranged to at least one of transmit and receive the second signal over a radiating near-field or EM far-field.

51. The hearing prosthesis of claim 48, wherein the antenna is arranged to operate simultaneously for transmitting or receiving the first signal and transmitting or receiving the second signal.

52. The hearing prosthesis of claim 48, wherein the medical device comprises a cochlear implant.

53. The hearing prosthesis of claim 48, wherein an upper end of the second RF band signals is below or equal to approximately 40 MHz.

* * * * *